(12) United States Patent
Loud

(10) Patent No.: US 7,109,704 B1
(45) Date of Patent: Sep. 19, 2006

(54) FLEXIBLE SHAFT WITH A HELICALLY WOUND DATA CABLE SUPPORTING A SMOOTH OUTER SLEEVE FOR EDDY CURRENT PROBE

(75) Inventor: Christopher R Loud, North Bend, WA (US)

(73) Assignee: Zetec, Inc., Issaquah, WA (US)

( * ) Notice: Subject to any disclaimer, the term of this patent is extended or adjusted under 35 U.S.C. 154(b) by 0 days.

(21) Appl. No.: 10/906,917

(22) Filed: Mar. 11, 2005

Related U.S. Application Data

(63) Continuation of application No. 10/271,813, filed on Oct. 16, 2002, now abandoned.

(51) Int. Cl.
*G01R 33/00* (2006.01)

(52) U.S. Cl. ..................................... 324/262

(58) Field of Classification Search ................ 324/262
See application file for complete search history.

(56) References Cited

U.S. PATENT DOCUMENTS

| | | | | |
|---|---|---|---|---|
| 3,267,369 A | * | 8/1966 | McLoad | ..................... 324/515 |
| 3,359,822 A | * | 12/1967 | Hurlow | ..................... 74/502.5 |
| 3,581,523 A | * | 6/1971 | Bartholomew | ................ 464/52 |
| 3,791,898 A | * | 2/1974 | Remi | .......................... 156/143 |
| 4,413,231 A | | 11/1983 | Amedro | |
| 4,883,946 A | * | 11/1989 | Jacquier | ..................... 219/523 |
| 5,174,164 A | | 12/1992 | Wilheim | |
| 5,174,165 A | | 12/1992 | Pirl | |
| 5,254,944 A | | 10/1993 | Holmes | |
| 5,279,168 A | | 1/1994 | Timm | |
| 5,669,383 A | | 9/1997 | Johnson | |
| 6,505,525 B1 | | 1/2003 | McGrew | |
| 6,526,114 B1 | | 2/2003 | Paillaman | |

\* cited by examiner

*Primary Examiner*—Reena Aurora
(74) *Attorney, Agent, or Firm*—David L. Tingey

(57) ABSTRACT

A flexible shaft of nonrigid components for use in pushing an eddy current probe through small diameter pipe bends includes a thin-walled flexible outer sleeve enclosing a data cable helically coiled around a central inner core, typically of braided wire. The inner core is functionally incompressible and inextensible to sustain compressive forces derived from pushing the shaft through a pipe. The outer sleeve supported from within by the data cable and the inner core for sustaining lateral forces of pusher rollers is longitudinally even and smooth to advance the shaft without damage to it.

14 Claims, 3 Drawing Sheets

FLEXIBLE SHAFT WITH A HELICALLY WOUND DATA CABLE SUPPORTING A SMOOTH OUTER SLEEVE FOR EDDY CURRENT PROBE

BACKGROUND

1. Field of the Invention

This invention relates to shafts for moving an eddy current probe through a pipe and, specifically, to a flexible shaft with an even, protective outer sleeve supported by a data cable helically wound around a solid inner core.

2. Prior Art

It is known to have an eddy current probe for remotely obtaining nondestructive measurements of the integrity of tubes in nuclear steam generators and heat exchangers. The eddy current probe is pushed through a tube or pipe by a flexible shaft to which it is attached on the shaft lead, or distal end, the shaft extending from the probe to a data recorder with data cables running along the shaft. As the shaft impels the probe into the pipe, the probe measures the pipe along the pipe length, transmitting probe measurement data through the data cables.

Because the nuclear industry heat exchanger pipes have a small bend radius, typically less than 2 inches, it has been difficult to inspect them because of the inflexibility of conventional shaft materials. Without the capability of negotiating small-radii bends, it becomes impossible to perform a full examination of the pipes from one pipe end to another, requiring multiple passes through the pipe from different pipe access locations. Completing a full pipe measurement then results in increased inspection time, increased radiological exposure to personnel setting up the measurement equipment and increased damage to measurement equipment.

Flexible shafts designed to protect data cables and sustain compressive forces of pushing have been tried with less than satisfactory results. The shafts typically have a structure that allows them to bend within a curved pipe and provide for data cables running with the shaft. The cables are often expensive to produce and cumbersome to use. Typically, the shaft outer structure also is incompatible with a probe pusher/puller device commonly used to insert the probe in a pipe. The probe pusher comprises a reel and one or more sets of opposing rollers between which the shaft passes. The motor-driven rollers engage the shaft and rotate to urge the shaft forward, unwrapping the shaft from around the reel. As the rollers engage the shaft with sufficient force to impel the shaft the rollers often damage the shaft structure.

There exist eddy current probes that are designed to rotate within a pipe causing drive and pickup coils to rotate with the rotating probe. Shafts are designed that can rotate the probe as the shaft pushes the probe along the pipe. A spinning motor rotates the shaft as probe pusher rollers drive the shaft into a pipe. These uneven shafts are that able to simultaneously rotate and push the probe typically comprise an uneven outer surface that do not smoothly engage the pusher rollers and are often destroyed as the rollers engage the uneven shaft.

It is a first object of the invention to provide a shaft for an eddy current probe that is not damaged by a probe pusher as the shaft is driven into a pipe. It is a second object that the shaft be rotatable by a spin motor as the probe pusher drives the shaft into the pipe without damage to the shaft. It is a third object that the shaft be sufficiently flexible to negotiate tight bends in pipes yet able to sustain compressive forces without buckling as it is pushed through the pipe.

SUMMARY OF THE INVENTION

These objects are achieved in a flexible shaft with an even outer sleeve that encloses an inner shaft structure. The outer sleeve is flexible to allow necessary small-radii bending while uniformly smooth and even and sufficiently rigid to protect the shaft from lateral forces of probe pusher rollers. Resistance to these lateral forces is primarily provided by the internal structure of the shaft as the outer sleeve broadly contacts and distributes lateral, or inwardly directed radial forces along the shaft internal structure.

The bendable outer sleeve is made of a lubric material, such as nylon, to facilitate sliding in a pipe and is generally thin-walled to facilitate bending and hence unable to sustain compressive forces of pushing. However, the outer sleeve may be enclosed around a prior eddy current probe shaft to add protection from damage from the probe pusher, therein preserving the functionality or advantage that might be offered by that prior shaft.

For simplicity and cost, ideally the shaft consists of its minimum essential elements: data cables enclosed by the outer sleeve together with a simple additional element that can sustain the compressive forces of pushing, reducing cost and adding reliability. In combination with the outer sleeve, a simplified inner structure includes data cables and a braided wire cable, typically of steel or brass as an axial core, that is bendable in off axis movement in yaw and pitch but inflexible axially. Similar braided wire cables are used in automotive speedometer cables, motorcycle clutch cables, and bicycle brake cables. Such a cable is flexible yet does not buckle under longitudinal compression forces. Over long cable lengths, the unconstrained wire cable may curl or coil but when closely confined within the outer sleeve there is inadequate space for it to do so. Instead, under compressive load, that is, when pushed from an end by a shaft pusher or otherwise, the wire cable bends to a pipe being tested, but the wire cable cannot buckle within the outer sleeve when the wire cable and the outer sleeve fill a substantial portion of the pipe.

The data cable typically comprises one or more coaxial cables helically coiled around the braided wire cable spacing the braided wire cable uniformly from the outer cable and preventing collapse of the shaft. A lubric sheath, such as a Teflon tube, surrounds the coaxial cable and braided wire shaft defining a shaft inner structure within the outer sleeve.

For purposes herein, the term "braided" is meant to include braided, woven, interlaced, twisted and all other forms of combining a plurality of small wires of little physical strength into a cable of increased tensile and compressive strength that has high deformation thresholds under strain or stress (push or pull) forces. A data cable means a cable containing one or more electrical conductors, such as a typical coaxial cable, that is flexible and bendable and alone unable to resist lateral forces without collapsing or moving position under even a moderate lateral force. An even outer surface means an outer surface smooth without variation, such as by a discontinuity or change in curvature such that cable pusher rollers can roll on the even outer sleeve smoothly longitudinal with the shaft, undisturbed by the surface, without causing a change in motion or position of the rollers, such as might occur with bumping or bouncing, as the shaft passes through the rollers. An outer surface running a given length means the described surface continues throughout the length without change or interruption.

DETAILED DESCRIPTION OF THE PREFERRED EMBODIMENT

Figure 1:
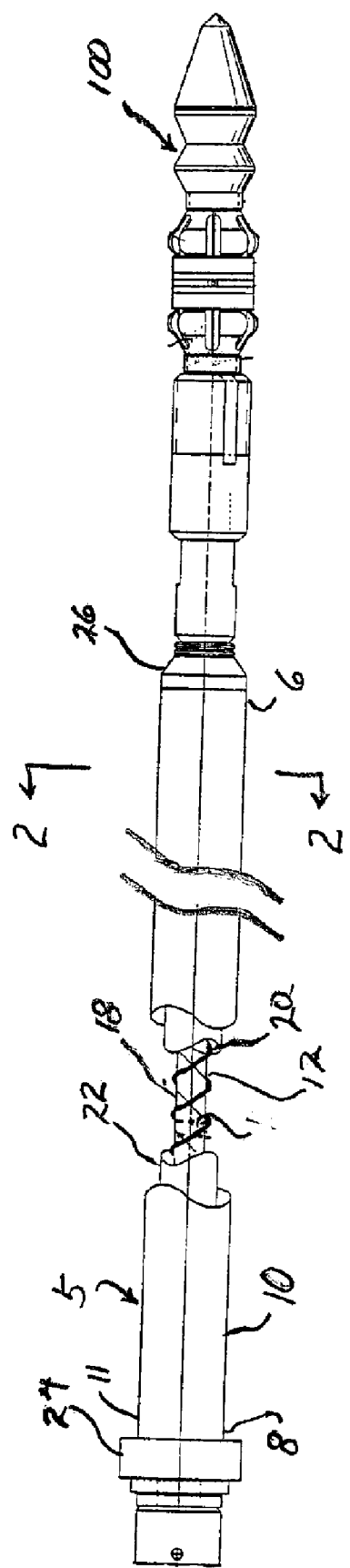
FIG. 1 is a side cut-away view of the flexible shaft with a probe attached.
Figure 2:
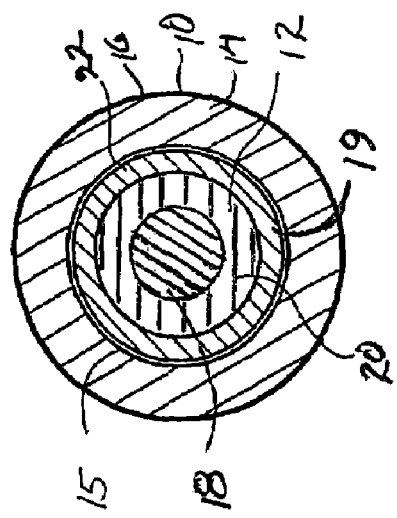
FIG. 2 is an end view of the flexible shaft of FIG. 1 along the transverse section line 2—2.
Figure 5:
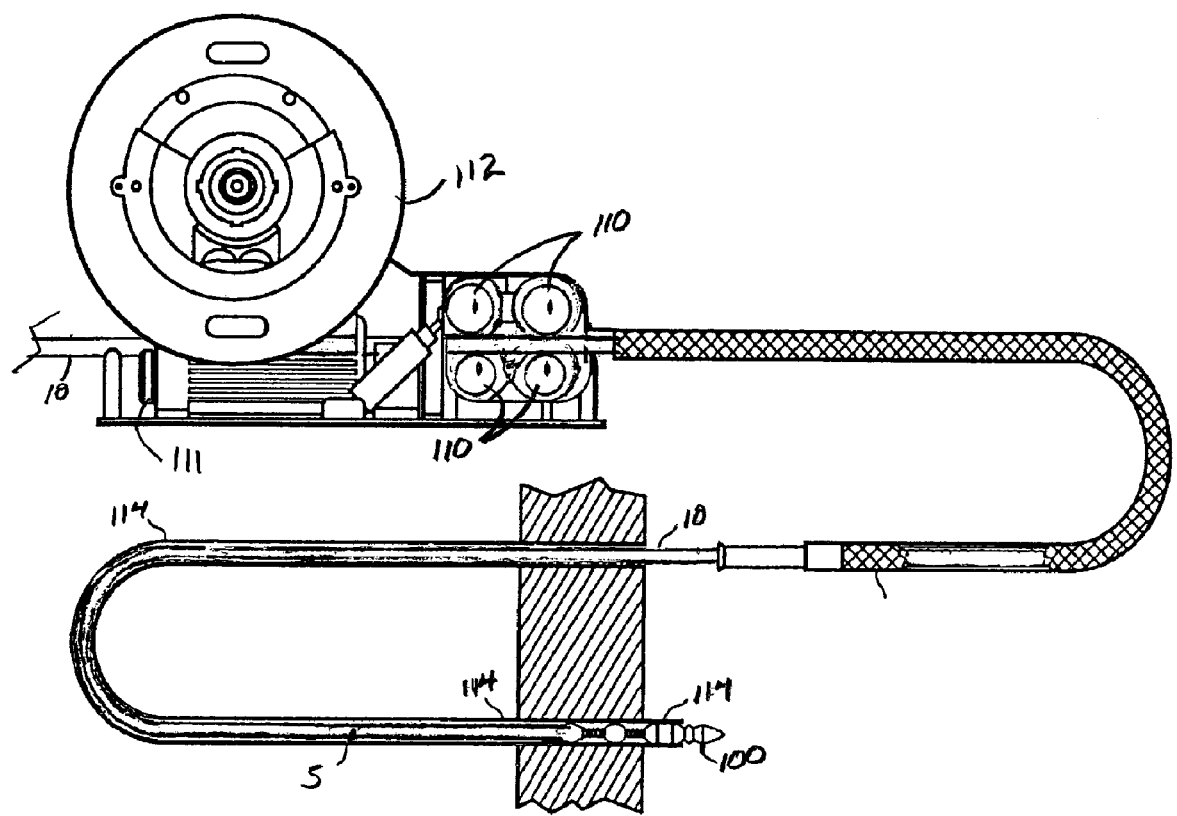
FIG. 5 is a side cross-sectional view of a shaft pusher with a reel used for transporting the shaft, and an unreeled shaft rotated by a spin motor as the shaft is engaged by rollers of the shaft pusher and driven through a tubular guide to a curved pipe and into the pipe

As shown in the figures and particularly in FIGS. 1 and 2, the flexible shaft 5 for an eddy current probe 100 that is secured to a shaft lead end 6 comprises a protective outer sleeve 10 outermost on the shaft running continuously through its length between the measuring device on the shaft lead end 6 and a shaft tail end 11 that closely fits around a shaft inner structure 12. The outer sleeve 10 comprises a continuous thin wall 14 with an inner surface 15 and a lubric outer surface 16 that is a longitudinally even and smooth outer surface such that rollers 110 from a shaft pusher 112 shown in FIG. 5 roll evenly and smoothly on the outer sleeve 10 while a spin motor 111 simultaneously rotates the shaft as it moves through the shaft pusher 112. The thin-walled outer sleeve 10, flexible in bending around a curved pipe 114, is characteristically unable to sustain lateral or longitudinal forces such as from pusher rollers, without deformation. The outer sleeve 10 becomes able to sustain lateral forces of the rollers 110 without collapse or deformation only when it is supported from within by the shaft inner structure 12. With support from the shaft inner structure, it is able to be thin-walled and flexible yet distribute lateral forces from the rollers 110 to the shaft inner structure 12 so the shaft 5 is not damaged by pusher rollers.

The outer sleeve 10 can be effectively used over many shafts of various designs to provide similar protection from shaft pullers and generally to protect an arbitrary shaft 116 from hostile environments. The arbitrary shaft when covered by the outer sleeve 10 becomes the shaft inner structure 12, able to sustain compressive forces from pushing the shaft and oppose side forces from the shaft pusher as distributed by the outer sleeve.

Figure 4:
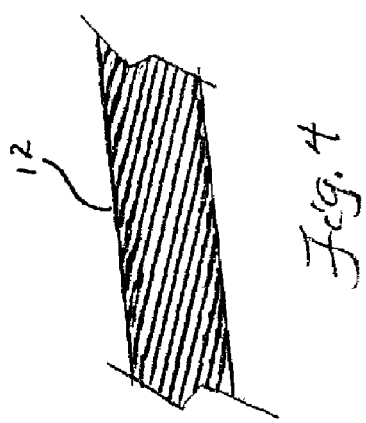
FIG. 4 is representative view of a flexible woven wire shaft.
Figure 3:
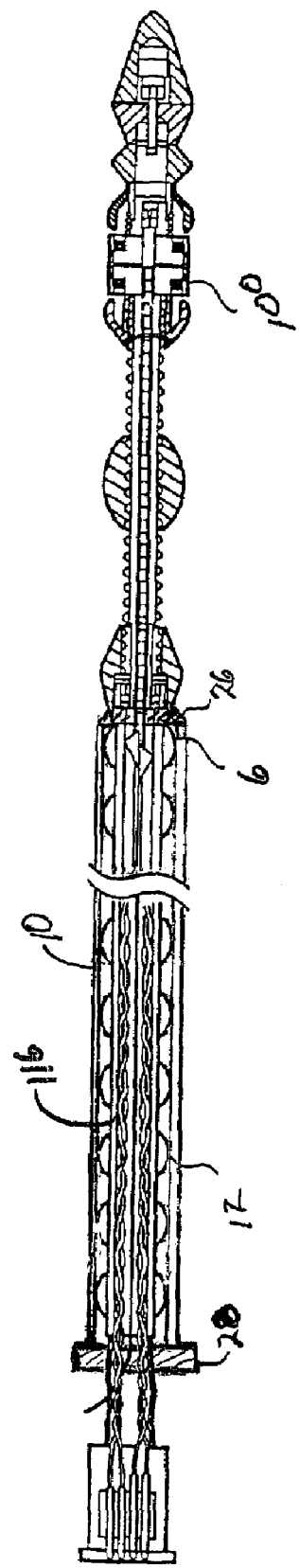
FIG. 3 is a cross-sectional view of an outer sleeve around an arbitrary eddy current probe shaft.

To sustain compressive forces of pushing, an inner core 18, typically braided wire cable shown in FIG. 4, flexible in transverse, or off axis bending, is axial in the inner shaft structure in lieu of prior cable structures 116 (see FIG. 3) forming a functionally axially incompressible and inextensible shaft. Typically, the inner core 18 is solid, that is, without a bore or cavity within, to better sustain external forces without collapsing. Thus, for purposes herein, the term "inner core" means a positive structure on the shaft axis (as opposed to a central bore or other axial void) itself functionally able to sustain without deformation longitudinal compression forces that are derived from pushing the shaft through the pipe.

A data cable 20, typically an electrically conducting coaxial cable, provides electrical communication from the eddy current probe through the shaft 5. The data cable or cables 20 are all outside the solid inner core 18 helically wound on and in contact with the wire cable 18 forming a radial structural connection between the inner core 18 and the outer sleeve 10. For these purposes, a radial structural connection between the inner core 18 and the outer sleeve 10 means a positive structural link that conveys physical radial forces on the outer sleeve 10 to the inner core 18. The data cable 20 is fundamental to radial structural connection in that it comprises the physical, or structural, link by which the radial forces on the outer sleeve 10 are transmitted to the inner core 18. The coaxial cable 20 is wound helically with winds spaced apart to facilitate bending of the inner core 18 yet sufficiently close to maintain the inner core 18 central within the outer sleeve 10 to prevent the inner core 18 from buckling within the outer sleeve 10. Thus wound, each small segment of the data cable 20 is effectively transverse to the shaft and therefore essentially does not flex when the shaft bends, which bending otherwise would characteristically strain the insulation of the data cable 20 and compromises the integrity of data transmitted on the data cable 20 if the cable were to run parallel with the shaft and bend with the shaft.

The shaft inner structure 12 closely fits in the outer sleeve 10. A lubric sheath 22 encloses the shaft inner structure 12 along on inner surface 15 of the outer sleeve wall 14. The lubric sheath 22 around the data cable 18 and in contact with the bendable outer sleeve 10 reduces friction and prevents wear between the coaxial cable 18 and the outer sleeve 10. Tape 19 may be used around the data cable 20 to keep it in place as the shaft is being assembled, and for ease of description may be deemed part of the outer sleeve 10. It is thus to be understood that the shaft comprises only nonrigid components, thus lending itself to small-radius bends throughout the shaft length, unlimited by dimensions and functional relations of rigid components.

It is understood that the helical winds of the coiled data cable 20 serve not only as the electrical signal conductor but also as a spacer structurally supporting and the outer sleeve 10 extending radially between the inner core 18 and the outer sleeve 10, structurally supporting the inner core 18 circumferentially and longitudinally, spacing the inner core 18 from the outer sleeve 10 and preventing the inner core 18 from buckling within the outer sleeve 10 while maintaining a constant distance between the inner core 18 and the outer sleeve 10. The inner core 18 therefore remains constrained, centered in the outer sleeve 10 by the data cable 20, the constraining structure further preventing the data cable 18 from buckling under compressive forces of pushing, maintaining the integrity of the shaft.

Because the flexible shaft 5 is intended to operate in an adverse environmental condition, the outer sleeve 10 is sealed on each end by end caps 24 and 26 fully encapsulating the shaft inner structure 12. The end caps also constrain relative longitudinal movement of the sheath 22 and braided wire cable 18 and coaxial cable 20 within the tube. Otherwise, the outer sleeve 10 and sheath 22 are unattached to permit unimpeded relative movement inherent in bending. The data cable 20 passes through the end caps 24 and 26 for connection to electrical connectors on shaft ends 6 and 8.

What is claimed is:

1. A flexible shaft having a length between a lead end and a tail end for moving a measuring device on the shaft lead end through a pipe, the improvement comprising,
   a flexible inner core functionally able to sustain without inner core deformation longitudinal compression forces that are derived from pushing the shaft through the pipe rollers, a data cable helically wound on and in contact with the inner core, a flexible outer sleeve outermost on the shaft with a longitudinally even outer surface running uninterrupted continuously between the shaft lead and tail ends, the outer sleeve enclosing the data cable and inner core and engaging the data cable in direct circumferential contact throughout the shaft length therein providing a radial structural connection between the outer sleeve and the inner core through the data cable such that rollers of a shaft pusher smoothly engage the even outer surface of the outer sleeve throughout the shaft length, with radial forces imparted from the rollers on the outer sleeve being conveyed to the inner core through the data cable, the outer sleeve thus sustained from collapsing by structural support provided by the inner core communicated to the outer sleeve through the data cable.

2. The flexible shaft of claim 1 wherein the outer sleeve is thin-walled and alone unable to sustain lateral forces of pusher rollers without deformation or collapse, the outer sleeve maintaining its even surface through said structural support of the helically-wound data cable and the inner core.

3. The flexible shaft of claim 1 wherein the outer sleeve comprises a lubric outer surface.

4. The flexible shaft of claim 1 wherein the data cable is helically wound around the inner core through the shaft length.

5. The flexible shaft of claim 1 wherein the helical winds of the helically wound data cable are spaced apart along the data cable.

6. The flexible shaft of claim 1 wherein all data cables are outside the inner core.

7. The flexible shaft of claim 1 wherein the inner core is without a bore or cavity within.

8. The flexible shaft of claim 1 wherein the outer sleeve further comprises a lubric sheath along an outer sleeve inner surface engaging the data cable, therein reducing friction between the data cable and the outer sleeve.

9. The flexible shaft of claim 1 wherein the inner core comprises a braided wire cable.

10. The flexible shaft of claim 1 wherein the helically wound data cable in spacing contact between the outer sleeve and the inner core secures the inner core central within the outer sleeve therein preventing the inner core from buckling within the outer sleeve.

11. The flexible shaft of claim 1 wherein mutually spaced-apart winds of the helically wound cable spacing the inner core from the outer sleeve are sufficient close to maintain the inner core central within the outer sleeve and prevent the inner core from buckling within the outer sleeve.

12. A flexible shaft having a length between a lead end and a tail end for moving a measuring device on the shaft lead end through a pipe, the improvement comprising, a flexible inner core, a data cable helically wound on and in contact with the inner core, a flexible outer sleeve outermost on the shaft with a longitudinally even outer surface running uninterrupted continuously between the shaft lead and tail ends, the outer sleeve enclosing the data cable and inner core and engaging the data cable in direct circumferential contact throughout the shaft length therein providing a radial structural connection between the outer sleeve and the inner core through the data cable such that as rollers of a shaft pusher smoothly engage the even outer surface of the outer sleeve throughout the shaft length, radial forces imparted from the rollers on the outer sleeve are conveyed to the inner core through the data cable, the outer sleeve thus sustained from collapsing by structural support provided by the inner core communicated to the outer sleeve through the data cable, wherein the data cable runs the length of the shaft, the helically wound data cable functionally maintaining spacing contact with the inner core and the outer sleeve through the length of the shaft, securing the inner core central within the outer sleeve therein preventing the inner core from buckling within the outer sleeve, thus enabling the inner core to sustain longitudinal compression forces that are derived from pushing the shaft through the pipe without deformation.

13. A flexible shaft having a length between a lead end and a tail end for moving a measuring device on the shaft lead end through a pipe, the improvement comprising, a solid but flexible inner core without an inner cavity functionally able to sustain longitudinal compression forces that are derived from pushing the shaft through the pipe without deformation and compression forces imparted radially from cable pusher rollers, a data cable helically wound on and in contact with the inner core spaced apart along the data cable through the shaft length, a flexible outer sleeve outermost on the shaft with a longitudinally even outer surface running uninterrupted continuously between the shaft lead and tail ends, the outer sleeve enclosing the data cable and inner core and engaging the data cable in direct circumferential contact throughout the shaft length therein providing a radial structural connection between the outer sleeve and the inner core through the data cable, such that as rollers of a shaft pusher smoothly engage the even outer surface of the outer sleeve throughout the shaft length, radial forces imparted from the rollers on the outer sleeve are conveyed to the inner core through the data cable, the outer sleeve thus sustained from collapsing by structural support provided by the inner core communicated to the outer sleeve through the data cable.

14. The flexible shaft of claim 13 wherein the outer sleeve further comprises a lubric sheath along an outer sleeve inner surface engaging the data cable therein reducing friction between the data cable and the outer sleeve.

* * * * *